United States Patent [19]
Askill et al.

[11] Patent Number: 5,855,208
[45] Date of Patent: Jan. 5, 1999

[54] METHODS FOR DRAPING SURGICAL INCISION SITES USING A BIOCOMPATIBLE PREPOLYMER

[75] Inventors: Ian N. Askill, Colorado Springs, Colo.; Richard J. Greff, St. Pete Beach, Fla.

[73] Assignee: MedLogic Global Corporation, Colorado Springs, Colo.

[21] Appl. No.: 941,097

[22] Filed: Oct. 8, 1997

[51] Int. Cl.⁶ .................................................. A61B 19/00
[52] U.S. Cl. ........................... 128/849; 424/402; 128/850
[58] Field of Search ................................... 128/849–856; 424/402, 78.35; 523/105, 111

[56] References Cited

U.S. PATENT DOCUMENTS

| Re. 31,886 | 5/1985 | Hodgson | 128/849 |
| Re. 31,887 | 5/1985 | Hodgson | 128/849 |
| 3,645,835 | 2/1972 | Hodgson | 602/54 |
| 5,730,994 | 3/1998 | Askill | 424/402 |

*Primary Examiner*—Michael A. Brown
*Attorney, Agent, or Firm*—Burns, Doane, Swecker & Mathis, L.L.P.

[57] ABSTRACT

Disclosed are methods for draping a surgical incision site prior to surgery. Specifically, the methods of this invention involve the in situ formation of a biocompatible polymeric drape over the skin surface at the surgical incision site. An incision is then made through this surface and the surgery is then conducted through the incision.

17 Claims, No Drawings

METHODS FOR DRAPING SURGICAL INCISION SITES USING A BIOCOMPATIBLE PREPOLYMER

BACKGROUND OF THE INVENTION

1. Field of the Invention

This invention is directed to methods for draping a surgical incision site prior to surgery. Specifically, the methods of this invention involve the in situ formation of a polymeric drape over a mammalian skin surface at the surgical incision site. An incision is made through the drape and surgery is then conducted through the incision.

2. References

The following publications, patent applications and patents are cited in this application as superscript numbers:

[1] Masterson, M. D., "Skin Preparation", Chapter 9, in Surgical Infections, Diagnosis and Treatment, Meakins, Ed., Scientific American, Inc., New York, USA, Publisher, pp. 119–125 (1994)

[2] Osuna, et al., "Comparison of an Antimicrobial Adhesive Drape and Povidone-Iodine Preoperative Skin Preparation in Dogs", Veterinary Surgery, 21(6):458–462 (1992)

[3] Hagen, et al., "A Comparison of Two Skin Preps Used in Cardiac Surgical Procedures", AORN Journal, 62(3):393–402 (1995)

[4] Alexander, et al., "Development of a Safe and Effective One-Minute Preoperative Skin Preparation", Arch. Surg., 120:1357–1361 (1985)

[5] Chiu, et al., "Plastic Adhesive Drapes and Wound Infection After Hip Fracture Surgery", Aust. N.Z. J. Surg., 63:798–801 (1993)

[6] Barley, U.S. Pat. No. 5,306,490, Methods for Retarding Blister Formation by Use of Cyanoacrylate Adhesives, issued Apr. 26, 1994.

[7] Barley, et al., U.S. Pat. No. 5,254,132, Methods for Treating Suturable Wounds by Use of Sutures and Cyanoacrylate Adhesives, issued Oct. 19, 1993

[8] McIntire, et al., U.S. Pat. No. 3,654,239, Process for the Preparation of Poly(α-Cyanoacrylates), issued Apr. 4, 1972

[9] Barley, et al., International Patent Application Publication No. WO 93/25196, Methods for Treating Non-Suturable Wounds by Use of Cyanoacrylate Adhesives, published Dec. 23, 1993

[10] Barley, et al., U.S. Pat. No. 5,653,789, Methods for Reducing Skin Irritation From Artificial Devices by Use of Cyanoacrylate Adhesives, issued Aug. 5, 1997

[11] Tighe, et al., U.S. Pat. No. 5,403,591, Methods for Inhibiting Skin Ulceration by Use of Cyanoacrylate Adhesives, issued Apr. 4, 1995

[12] Tighe, et al., U.S. Pat. No. 5,580,565, Use of Cyanoacrylates for Providing a Protective Barrier, issued Dec. 3, 1996.

[13] Ritter, et al., "Retrospective Evaluation of an Iodophor-Incorporated Antimicrobial Plastic Adhesive Wound Drape", Clinical Orthopedics and Related Research, pp. 307–308 (1988)

[14] Duhaime, et al., "Distribution of Bacteria in the Operating Room Environment and its Relation to Ventricular Shunt Infections: a Prospective Study", Child's Verv. Syst., 7:211–214 (1991)

[15] Modern Plastics Encyclopedia (1997)

All of the above publications, patent applications and patents are herein incorporated by reference in their entirety to the same extent as if each individual publication, patent application or patent was specifically and individually indicated to be incorporated by reference in its entirety.

3. State of the Art

Reducing morbidity and/or infection associated with surgical procedures necessitates the thorough preparation of the patient's skin prior to initiating any incision into the skin as part of the surgical procedure. The primary reason for patient skin preparation is to reduce the risk of wound infection by introduction of microbes into the incision site[1] from either skin microbes or from air borne microbes.[14] In turn, reduction in such risk correlates, obviously, with reductions in the population of microbes on the skin surface and especially at the skin surface adjacent to the incision site.

Suitable skin preparation involves, for example, application of an antimicrobial agent onto and around the skin surface adjacent to the incision site which reduces the population of microbes on these surfaces and, hence the relative risk of infection. However, the skin is never completely sterilized during these procedures and microbes from hair follicles and sweat/sebaceous glands will migrate to the surface of the skin thereby raising microbial populations and accordingly relative infection risks.[2] To counter possible microbial migration into the incision, it has become common practice to employ a surgical incise drape over the patient's incision site.

Conventional surgical incise drapes include those which comprise preformed, sized polymeric films coated with a pressure-sensitive adhesive. In some cases, an antimicrobial agent is incorporated directly into the adhesive in order to permit a continuous release of the antimicrobial agent onto the skin.[3,13] After application of an antimicrobial agent onto the skin surface of the patient, the surgical incise drape is applied, adhesive side down, with pressure to effect adherence of the drape to the skin. A surgical incision is then made through the drape and the requisite surgery is conducted through this incision. After completion of the surgery, the drape is conventionally removed from the skin surface prior to final incision closure.

Notwithstanding the benefits associated with a surgical incise drape, several problems exist which have both limited the general applicability of these drapes to all surgical incisions and have actually increased the relative risk of infection. Specifically, the first most common and potentially serious problem associated with the use of conventional surgical incise drapes is the separation or lifting of the drape from the skin surface during surgery. In one study, it was reported that up to 44% of the drapes experienced at least partial separation during human surgery[2]. In turn, Alexander, et al.[4] report a six-fold increase in infection rates in operations in which the surgical incise drape separated from the skin during surgery as compared to infection rates in which the drape did not separate from the skin. Without being limited by any theory, it is generally believed that occlusion of the skin by the surgical incise drape provides a moist, warm skin surface which encourages microbial growth. It is further believed that separation of the drape from the skin during surgery permits migration of microbes and/or microbial growth at these sites and, accordingly, in such cases, the use of a drape actually promotes rather than retards microbial populations at the incision site.

Non-adherence of the surgical incise drape to the patient's skin is, of course, related to adhesive failure as well as wrinkling of the preformed polymeric film during application. In the former case, this has lead to some attempts to increase the amount and/or strength of adhesive employed in the drape to secure the drape to the mammalian skin surface. However, this in turn may lead to more rather than fewer complications. In particular, since the drape is conventionally removed from the skin shortly after surgery by, e.g., the peeling or pulling off of the drape, an increase in the relative strength of the adhesive leads to increased difficulty in removing the drape from the skin. The effort required to effect removal can also lead to skin tearing and irritation, especially adjacent to the incision site, as well as removal of hair. Skin tearing is clearly disadvantageous and invariably raises additional infection risks because the mammalian skin surface is open (compromised) and therefore susceptible to infection. Moreover, the removal of hair (shaving) has also been associated with increased infection rates[2] and hair removal due to adhesive/drape removal from the mammalian skin can also be expected to provide similar increased infection rates.

In the latter case, wrinkling of the polymeric drape is essentially irreversible because the wrinkles cannot be smoothed out absent complete removal of the drape and drapes, once removed, typically cannot be reapplied to the skin. Additionally, air pockets found in the wrinkles of such drapes are undesirable because they provide a source of microbes adjacent to the skin and, in some cases, promote microbial growth. Wrinkling of the polymeric film is common to most applications of the surgical incise drapes but is particularly problematic with contoured surfaces such as elbows, knees, bony hips, etc. This, in turn, has limited the use of such conventional drapes.

An additional problem associated with preformed polymeric films used as surgical incision drapes arises because such drapes do not conform well to three dimensional contours of the human body thereby increasing the likelihood of separation during surgery. For example, while abdominal areas through which the surgical incision is to be made are typically good candidates for conventional surgical incise drapes, other surfaces such as elbow, knee, foot, and bony hip surfaces (as examples) have three dimensional contours which render consistent adherence of the drape over the incision site during surgery problematic at best. In this regard, Chiu, et al.[5] report that the use of sterile adhesive drapes during hip fracture surgeries appeared to have actually encouraged microbial accumulation in the skin adjacent to the wound.

Still a further problem arises from the fact that many adhesives employed with preformed polymeric films do not adhere well to hair thereby limiting their utility[2]. Additionally, as noted above, shaving to remove hair prior to surgery has been clinically associated with increased wound infection rates.

In an alternative embodiment, the art has proposed formation of surgical incise drapes by the use of emulsions/solutions containing a volatile organic solvent and a polymer. Upon application to the skin, the solvent dissipates leaving a polymeric film which acts as the incise drape. Significant problems exist with such a procedure and, in particular, the polymeric film lacks strong adhesion to the skin and the volatile solvent can create irritation (e.g., skin, nose, etc.) as well as can be the source of a fire hazard in the operating room.

Lastly, while the most important purpose of using surgical incise drapes is to prevent postoperative wound infections, the simple fact of the matter is that the drapes of the prior art are removed shortly after surgery and there is, accordingly, no postoperative antimicrobial effect available to the skin surface at the surgical incision site.

This invention is directed, in part, to the discovery that the in situ formation of a biocompatible polymeric drape at the surgical incision site prior to surgery by application of a biocompatible prepolymer composition overcomes many of the prior art problems associated with the use of conventional surgical incise drapes and additionally provides incremental advantages heretofore not achieved by conventional drapes. For example, certain of the prepolymers described have bacteriostatic properties and, in any event, the prepolymers permit the inclusion of compatible antimicrobial agents if such is desired. Still another advantage is the formation of an appropriately configured drape without the need to modify the dimensions provided with commercial preformed polymeric drapes. Still further, the methods of this invention result in incise drapes which mold directly to the multiple contours of the intended surgical site.

The use of biocompatible prepolymers per this invention is in contrast to known uses of prepolymers, such as cyanoacrylates, as alternatives or adjuncts to sutures[7] or as hemostatic agents[8]. Other described uses of cyanoacrylate prepolymers include their use in preventing friction blister formation[6], treating small non-suturable wounds[9], and in inhibiting surface skin irritation arising from friction between the skin surface and artificial devices such as tapes, prosthetic devices, casts, and the like.[10] Still further cyanoacrylate prepolymers have been used to inhibit formation of decubitus ulcers[11] and in the prevention of skin irritation due to incontinence.[12]

SUMMARY OF THE INVENTION

This invention is directed to methods for draping a surgical incision site by application of a biocompatible prepolymer composition to the surface of the surgical incision site.

In situ polymerization of the biocompatible prepolymer composition provides for an adherent polymeric film over the surgical incision site which acts as a surgical incise drape during subsequent surgery. The biocompatible prepolymer composition can be applied as a liquid/gel to the skin surface which permits formation of an adherent film over any skin contour including elbows, knees, hips, and the like.

Since the polymeric film is naturally shed from the skin surface 1–4 days after application, there is no need to effect removal of the drape after surgery or cause the skin trauma potentially associated with drape removal. Moreover, in a preferred embodiment, the biocompatible prepolymer composition is formulated to contain an antimicrobial agent which, over time, will be released from the resulting film thereby providing for peri- and post-surgical infection protection not now available from conventional drapes.

Accordingly, in one of its method aspects, this invention is directed to a method for forming an adherent, surface conforming drape at a surgical incision site of a patient which method comprises:

(a) defining a surgical incision site on the patient;
(b) applying a sufficient amount of a composition comprising a polymerizable biocompatible prepolymer to the skin surface at the surgical incision site defined in (a) above so as to cover this site with the composition;
(c) polymerizing the biocompatible prepolymer so as to form a flexible, waterproof, polymer layer which adheres to the area(s) where the composition was applied; and
(d) creating an incision through the polymer layer formed in (c) above with the proviso that the biocompatible prepolymer in said composition is not a cyanoacrylate prepolymer.

Application of the composition comprising the polymerizable biocompatible prepolymer is preferably made onto the surface of intact or injured skin and the incision is made subsequent to formation of the polymer layer. More preferably, the intact skin is further characterized as lacking any infection, open wounds, etc. which would permit the polymer to penetrate from the surface of the epidermis to or beyond the dermal layer.

Preferably, the polymerizable biocompatible prepolymer is selected from the group of prepolymers consisting of urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, silicone, styrene, α-methyl styrene, vinyl acetate, one and two component epoxy materials, mixtures thereof, and the like.

In another preferred embodiment, the film of polymerized biocompatible prepolymer composition has a thickness of no more than about 1 millimeter and, more preferably, the polymer layer has a thickness of from about 2 to about 500 microns and still more preferably from about 20 to about 100 microns.

DETAILED DESCRIPTION OF THE PREFERRED EMBODIMENTS

This invention is directed to methods for draping a surgical incision site prior to surgery. However, prior to discussing this invention in further detail, the following terms will first be defined.

Definitions

As used herein, the following terms have the following meanings:

The term "surgical incision site" refers to the skin surface to which the surgical incision is to be made as well as the immediate area adjacent to the incision. This immediate area typically extends at least 0.1 to 2 inches (0.254 to 5.08 cm) in all directions beyond the incision and preferably extends by about 0.25 to 12 inches (0.635 cm to 30.48 cm) beyond the incision.

The term "incision" or "surgical incision" refers to any surgical penetration which extends beyond the dermal or epidermal layer of the patient's skin and includes, by way of example, incisions or punctures made by needles, knives (including surgical knives, surgical cautery knives, and the like), lasers (medical surgical laser), trocars, IV punctures, blood transfusion/donation punctures, vaccine inoculation punctures, medicament punctures (e.g., insulin injections), punctures associated with hemodialysis, etc.

The term "polymerizable biocompatible prepolymer compositions" refer to compositions comprising polymerizable monomers, oligomers or mixtures thereof including single or multi-component systems. The prepolymer composition will polymerize in situ on mammalian skin to form an adherent, water-insoluble polymeric layer over the skin. The prepolymer and resulting polymeric film are biocompatible with the skin as measured by the lack of moderate to severe skin irritation and the resulting polymer film is substantially non-toxic and can be removed from the skin by conventional means, e.g., sloughing off with the epidermal layer of the skin.

Included within the term "polymerizable biocompatible prepolymer compositions" are both single and multi-component systems. Single component prepolymer compositions include those wherein a single prepolymer is capable of polymerizing under suitable polymerization conditions (e.g., free radical conditions) to provide for a polymer film on mammalian skin. Such single component systems include well known reactive vinyl groups which form a biocompatible polymer such as urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, silicone, styrene, α-methyl styrene, vinyl acetate, and the like. Additionally, such single component systems can also comprise polymerization inhibitors, polymerization initiators, colorants, perfumes, etc.

Multi-component prepolymer compositions include those wherein two or more components are employed to co-react under suitable polymerization conditions to provide for a polymer film on mammalian skin. An example of a two component system is a diepoxide and a diamine specifically exemplified by bis-phenol A diglycidyl ether and ethylene diamine.

Preferred prepolymers for use in this invention include, by way of example only, urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, styrene, α-methyl styrene, vinyl acetate, one and two component epoxy materials, mixtures thereof, and the like. Mixtures of such prepolymers can also be employed.

Specifically excluded from such prepolymers are cyanoacrylate prepolymers whose use in forming incise drapes in situ are described in commonly assigned U.S. patent application Ser. No. 08/781,279 filed Jan. 10, 1997 which application is incorporated herein by reference in its entirety.

The polymerizable biocompatible prepolymers described herein polymerize on mammalian skin tissue without causing histotoxicity or cytotoxicity.

Such polymerizable biocompatible prepolymers are sometimes referred to herein as "prepolymers" and compositions comprising such are sometimes referred to herein as "prepolymer compositions".

The term "biocompatible plasticizer" refers to any material which is soluble or dispersible in the prepolymer composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in Modern Plastics Encyclopedia[15] the disclosure of which is incorporated herein by reference in its entirety. Specific plasticizers include, by way of example only, citrate plasticizers, phthalate plasticizers, and the like.

The term "polymerization inhibitor" refers to well known free radical inhibitors of prepolymers including materials such as hindered phenols, hydroquinone, 4-methoxyphenol, amines and the like. The polymerization inhibitor is typically employed in amounts effective to inhibit polymerization of the prepolymer composition until application of the composition onto the mammalian skin and initiation of polymerization as herein described. Preferably, the polymerization inhibitor is employed from about 0.01 to about 0.1 weight percent based on the total weight of the composition.

The term "initiator" refers to those well known polymerization initiators which are typically incorporated into the composition to initiate polymerization of the prepolymer. Such initiators include, by way of example, thermal initiators, light activated (e.g., UV) initiators, and the like. Examples of thermal initiators include peresters, peroxycarbonates, peroxides, azonitrile compounds, and the like. Promoters or accelerators such as metal salts and amines may be used with the initiators. The specific thermal initiator is preferably selected to initiate polymerization of the prepolymer at ambient skin temperatures (e.g., ~35° C.) or slightly above with additional heating.

Examples of light activated initiators include benzoin alkyl ethers, benzophenone, Darocur 1173 (available from Ciba Geigy, Ardsley, N.Y., U.S.A.), camphorquinone, and the like.

Preferably, the initiator is a light activated initiator and, after application of the prepolymer composition to mammalian skin, a light source is passed over the skin to initiate polymerization. Even more preferably, the light activated initiator is biocompatible with the skin as measured by the lack of moderate to severe skin irritation.

The term "surgical incision drape" refers to the drape formed over the surgical incision site and through which the surgical incision is made. The term surgical incision drape is synonymous with the term "incise drape" as used by Osuna, et al.[2]

The term "antimicrobial agent" refers to agents which destroy microbes (i.e., bacteria, fungi, yeasts and viruses) thereby preventing their development and their pathogenic action.

Methods

The methods of this invention comprise the in situ formation of a biocompatible polymeric film on the skin surface at the surgical incision site of a patient which polymeric film acts as a surgical incision drape.

The surgical protocol preferably involves skin preparation prior to in situ formation of the biocompatible polymer drape over the surgical incision site. Specifically, an antimicrobial agent is applied to the cleaned surgical incision site. The antimicrobial agent can be any suitable agent including iodine based solutions, alcohols, etc. In one embodiment, an iodine prep solution is first applied to the surgical incision site. The patient's skin is then cleansed and scrubbed with this solution and subsequently washed off. Afterwards, an alcohol solution or a povidone-iodine solution is applied to the surgical incision site to complete the skin preparation.

The surgical incision site is preferably dried and then an adherent polymeric drape is formed over this site by applying a biocompatible prepolymer composition to the skin surface at the surgical incision site. As noted above, this composition comprises polymerizable biocompatible monomers and/or reactive oligomers. If necessary a polymerization initiator can be included in the composition or applied onto the skin prior to application of the biocompatible prepolymer composition. Alternatively, polymerization can be initiated by light and polymerization is conducted at the appropriate time by passing a source of light over the patient's skin after application of the prepolymer composition.

Polymerization preferably occurs at ambient skin temperature while maintaining the skin surface under suitable conditions to allow polymerization to proceed. In general, the particular length of time required for polymerization will vary depending on factors such as the amount of composition applied, the temperature of the skin, the type (if any) of polymerization initiators used, and the like. However, in a preferred embodiment, polymerization is generally complete within about 0.5 to about 5.0 or more minutes while the skin is maintained at ambient conditions. During this period, the patient is maintained in a position which permits the biocompatible prepolymer to polymerize and form a polymeric drape while minimizing any patient movement which might dislodge the biocompatible prepolymer from that surgical incision site or create undesirable bonding.

Sufficient amounts of the composition are employed to cover (i.e., coat) the entire surgical incision site with a layer of the biocompatible prepolymer. If necessary, excess biocompatible monomer and/or oligomer can be removed from the skin with a wipe or tissue paper before polymerization or, after polymerization, any polymer formed at unintended sites can be removed with a suitable solvent (e.g., acetone—nail polish remover).

After polymerization, the resulting polymeric film forms a surgical incise drape which adheres to the skin, is flexible and waterproof. Such adherence effectively reduces the possibility that the drape will separate from the patient's skin during surgery. However, notwithstanding such adherence, the polymeric film defining the drape will only adhere to the skin for a period of about 1–4 days after which time it sloughs off. This occurs because the biocompatible polymer adheres only to the uppermost portion of the epidermal layer which is continuously in the process of being sloughed off and replaced by the underlying cells. Accordingly, the polymeric drape need not be removed in the manner of conventional drapes whose removal can result in skin trauma.

The polymeric drape should be maintained in an unbroken manner over the entire surgical incision site. This can be assured by careful application of the biocompatible prepolymer composition onto the skin. Additionally, the use of a plasticizer will facilitate the maintenance of the polymeric drape in an unbroken manner and will inhibit cracking of the drape.

In one embodiment, after application of the initial polymeric layer, a second, preferably thinner, layer is applied thereto. Additional amounts of biocompatible prepolymer composition can be applied as needed to maintain an unbroken coating covering over the surface skin areas.

Application is conducted under conditions wherein the polymeric drape has a thickness of no more than about 1 millimeter and, more preferably, the polymer layer has a thickness of from about 2 to about 500 microns and still more preferably from about 20 to about 100 microns. If thinner polymeric drapes are desired, then the polymeric drape should have a thickness of from about 2 to about 50 microns and preferably from 10 to 40 microns. The amount of biocompatible prepolymer composition applied to a unit area of skin to obtain such thicknesses is well within the skill of the art.

Once the polymeric surgical incise drape is formed over the surgical incision site (which as defined above includes the areas adjacent to the incision site), the polymeric surgical incise drape can then optionally be overdraped with sterile towels and sheets. In this optional embodiment, such towels and sheets are laid over (i.e., overdrape) the surgical incision drape to define a limited field of the surgical incise drape in which the actual incision is to be made and the subsequent operation is to be conducted.

In either case, the surgical incision is made through the polymeric surgical incise drape. Any conventional incision can be made including those created by needles, knives (including surgical knives and surgical cautery knives), lasers, trocars, and the like. The particular incision made is not critical and is, of course, made relative to why the incision is created (e.g., surgery).

Once the incision is made, the surgery or other procedure is conducted using conventional methods. Upon completion of the surgery, the surgical wound is closed by conventional methods. In one embodiment, however, closure of the epidermal or dermal layer of the surgical wound can be accomplished by application of the biocompatible prepolymer or a cyanoacrylate composition onto one or both of the opposing skin sections and maintaining contact between these skin sections until the biocompatible prepolymer has polymerized.

The size and thickness of the polymeric drape formed onto the skin surface area can be readily controlled by the amount and viscosity of the biocompatible prepolymer composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the biocompatible prepolymer composition in a controlled dropwise manner. Other methods for the controlled dispersement of the biocompatible prepolymer composition include, by way of example, a spray applicator, brush, wipe, swab or solid paddle applicator, applicators for repeated and intermittent use of the biocompatible prepolymer composition and the like.

In applicators, the biocompatible prepolymer composition is stored at ambient conditions and can be sterilized as needed.

Because the biocompatible polymer layer is waterproof, the patient is not prevented from bathing or being bathed and other activities involving exposure to water during the period the polymer layer protects the surgical incision site provided a further application of the prepolymer is made and then cured over the incision site.

Compositions

The biocompatible prepolymer compositions comprising the polymerizable prepolymers are prepared by conventional methods of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin application. Contrarily, where application is to be made to a specific position on the skin (e.g., elbow surfaces), higher viscosity materials are preferred to prevent "running" of the material to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the biocompatible prepolymer employed in these composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like, with PMMA being preferred. Fumed silica is particularly useful in producing a gel for topical application having a viscosity of from about 1500 to 50,000.

Thickening agents are deemed to be biocompatible if they are soluble or dispersible in the composition and are compatible with the skin as measured by the lack of moderate to severe skin irritation.

The biocompatible prepolymer compositions may optionally include a biocompatible plasticizer and such plasticizers are preferably included in the composition from about 10 to 40 weight percent and more preferably from about 20 to 30 weight percent based on the total weight of the composition absent any antimicrobial agent.

Additionally, the prepolymer compositions described herein preferably include a polymerization inhibitor and a polymerization initiator in effective amounts to provide for in situ polymerization on mammalian skin. For example, an effective amount of a polymerization inhibitor is preferably included in the composition to inhibit premature polymerization of the composition. Likewise, the polymerization initiator is included in the composition in effective amounts to initiate polymerization when the composition is placed under polymerization conditions (e.g., light). As above, such initiators include thermal initiators, light activated initiators and the like and in situ polymerization of the prepolymer composition on mammalian skin preferably occurs within 0.5 to 5 minutes.

The polymerizable biocompatible prepolymer compositions may additionally contain one or more optional additives such as colorants, perfumes, rubber modifiers, modifying agents, etc. In practice, each of these optional additives should be both miscible and compatible with the biocompatible prepolymer composition and compatible with the resulting polymer. Compatible additives are those that do not prevent the use of the biocompatible prepolymers in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

In a particularly preferred embodiment, the biocompatible prepolymer composition further comprises an antimicrobially effective amount of a compatible antimicrobial agent. Such compositions preferably comprise from about 10 to about 40 and preferably 10 to 30 weight percent of the compatible antimicrobial agent either as a solution or as a suspension based on the total weight of the composition. Compatible antimicrobial agents are those which are either soluble or suspendable in the biocompatible prepolymer composition, which do not cause premature polymerization or prevent polymerization of the biocompatible prepolymer composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., U.S.A. When povidone-iodine is employed in the biocompatible prepolymer composition, it is preferably from about 10 to about 40 weight percent and more preferably from about 10 to 25 weight percent is added to the biocompatible prepolymer composition based on the total weight of the composition.

Compositions comprising povidone-iodine and polymerizable cyanoacrylate esters are described by Greff, et al., in allowed U.S. patent application Ser. No. 08/781,409, filed Jan. 10, 1997, entitled "Cyanoacrylate Compositions Comprising an Antimicrobial Agent", which application is incorporated herein by reference in its entirety.

Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like. Still other suitable antimicrobial agents include anti-microbial chlorhexidine salts (e.g., chlorhexidine gluconate), silver, silver salts (e.g., silver sulfadiazine), silver oxide and the like. Preferably, however, the iodine containing polymer is povidone-iodine which is commercially available from a number of sources.

The use of a compatible antimicrobial agent in the composition permits the agent to be released from the polymeric drape thereby reducing microbial growth under the drape during surgery. Additionally, since the drape is maintained over the surgical incision site for 1–4 days after surgery, the release of antimicrobial agent further provides post-surgical anti-infection benefits.

Utility

The methods described herein are useful in forming a polymeric surgical incise drape over the surgical incision site of a mammalian patient. The polymeric drape finds particular utility in inhibiting microbial contamination of the incision during surgeries conducted on such patients. Such mammalian patients preferably include humans as well as domestic animals such as horses, cows, dogs, sheep, cats, etc. The maintenance of the polymeric film over the surgical incision after completion of the surgery is expected to reduce the incidence of infection by inhibiting microbial contamination of the incision.

The following examples illustrate certain embodiments of the invention but are not meant to limit the scope of the claims in any way.

EXAMPLES

In the examples below, all temperatures are in degrees celsius (unless otherwise indicated) and all percents are weight percent (also unless otherwise indicated) except for percent inhibition which is true mathematical percentage. Additionally, the following abbreviations have the following meanings. If an abbreviation is not defined, it has its generally accepted meaning.

| CFU | = | colony forming units |
|---|---|---|
| $cm^2$ | = | square centimeters |
| conc. | = | concentration |
| flex. | = | flexibility |
| dur. | = | durability |
| g | = | grams |
| min. | = | minutes |
| ml | = | milliliters |
| mm | = | millimeters |
| ppm | = | parts per million |
| $PVP-I_2$ | = | polyvinylpyrrolidone iodine complex |
| SAB-DEX | = | Sabouraud Dextrose |
| TSA | = | trypticase soy agar |

Example 1

This example illustrates the preparation of a prepolymer composition comprising $PVP-I_2$ as the antimicrobial agent. In this example, ambient conditions were employed unless otherwise noted.

Specifically, a prepolymer composition which could be used in the methods of this invention was prepared by combining a diepoxide resin (45 weight percent based on the total weight of the composition, available under the tradename Master Mend resin (60 second cure) from Loctite Corporation, Rocky Hill, Conn., U.S.A.) with $PVP-I_2$ (10 weight percent based on the total weight of the composition, available from Aldrich Chemical Company, Milwaukee, Wis., U.S.A.). The resulting mixture was stirred until homogeneous. To this mixture was added a diamine hardener (45 weight percent based on the total weight of the composition, available under the tradename Master Mend epoxy hardener—60 second cure time, from Loctite Corporation, Rocky Hill, Conn., U.S.A.) which composition was then mixed until homogeneous to provide for an antimicrobial prepolymer composition.

Example 2

This example illustrates in vitro application of a composition prepared similar to that of Example 1, except that the composition contains 47.5 weight percent of the diepoxide, 47.5 weight percent of the diamine hardener and 5 weight percent of the $PVP-I_2$ all based on the total weight of the composition.

Specifically, the above composition was applied to a Parafilm sheet and then spread to obtain a thin film of approximately 2–6 mm in thickness. The cure time and other observations were recorded and are set forth in Table I below:

TABLE I

| Cure Time | Film Area | Film formed | Flexibility of film | Adhesion of film |
|---|---|---|---|---|
| 3 min. | 6 $cm^2$ | YES | Very good | Very good |

The thickness of the film resulted in observable heat being generated during the exothermic polymerization reaction which was attributable to the thickness of the film and the large quantities of reagents in close proximity thereto.

Example 3

This example illustrates a further in vitro application of the composition prepared similarly to that of Examples 1 and 2 to form a polymeric film. In this Example, the composition was prepared using 3.0012 g of Master Mend epoxy resin, 0.3071 g of $PVP-I_2$, and 3.0251 g of Master Mend epoxy hardener.

Specifically, the composition of this Example was then applied to a Parafilm sheet and then spread to obtain a thin film of less than 1 mm in thickness both for the applied film and cured film. The cure time and other observations were recorded and are set forth in Table II below:

TABLE II

| Cure Time | Film Area | Film formed | Flexibility of film | Adhesion of film |
|---|---|---|---|---|
| 5 min. | 25.5 $cm^2$ | YES | Very good | Very good |

In this example, no appreciable heat was noted during the polymerization reaction. This was attributed to the fact that a thin film was employed which did not result in high concentrations of reagents in a given volume.

Additionally, the cure time for the compositions of each of Examples 2 and 3 corresponds substantially to the cure time for a similar composition containing no PVP-$I_2$ and, accordingly, the PVP-$I_2$ is deemed compatible with this two component prepolymer composition.

Example 4

This example illustrates in vivo application onto mammalian skin of a prepolymer composition similar to that of Example 2 and demonstrates how a surgical incise drape could be formed in situ on the skin.

Specifically, following the procedure of Example 2 above, a two component antimicrobial prepolymer composition was prepared which composition contained PVP-$I_2$. Approximately 2 g of this composition was applied onto the upper arm of a human male subject using a flat metal blade to spread the mixture into a smooth, flat film. The brownish film cured tack-free in about 2 minutes with a slight warming sensation under the film. The film remained intact on the upper arm for about 36 hours including exposure to two showers and an ocean swim. During this time, there was some lifting along the edge of the film. After about 36 hours, the film came off the upper arm in a single piece, about 5 mils thick. The skin theretofore under the film was normal in appearance with no redness or irritation.

Example 5

This example illustrates the preparation of another prepolymer composition which could be used in the methods of this invention which composition employed PVP-$I_2$ as the antimicrobial agent. In this example, ambient conditions were employed unless otherwise noted.

Specifically, camphorquinone (0.5130 g, available from Aldrich Chemical Company, Milwaukee, Wis., U.S.A.) was combined with trihexyl-O-acetylcitrate (20.1781 g, available from Aldrich Chemical Company, Milwaukee, Wis., U.S.A.). The resulting composition was mixed until the camphorquinone was dissolved. This composition is later referred to as "Composition A".

At this time, acrylate urethane prepolymer (78.0605 g, available under the tradename Loctite 3104 from Loctite Corporation, Rocky Hill, Conn., U.S.A.) was mixed with dimethylamino ethylacrylate (2.0036 g, available from Aldrich Chemical Company, Milwaukee, Wis., U.S.A.) and this mixture was then placed into a darkened room, the flask was covered with aluminum foil and a magnetic stirrer was added. This composition is later referred to as "Composition B".

Composition A was then added to Composition B in the darkened room with mixing until homogeneous to provide for "Composition C" which is a prepolymer composition lacking an antimicrobial agent.

A small portion (1–3 drops) of Composition C was placed between two sheets of Parafilm and exposed to bright white light from a projector bulb. The curing time for this composition was then measured. This test was repeated 3 times and the composition provided a reproducible cure time of about 10–15 seconds.

To composition C was added PVP-$I_2$ (20.1510 g, available from Aldrich Chemical Company, Milwaukee, Wis.). The resulting mixture was stirred in the darkened room until homogeneous. Then 1–3 drops of the resulting composition were placed between two sheets of Parafilm and cured as above. The curing time for this composition was then measured. This test was repeated for a total of 3 runs and the composition provided a reproducible cure time of about 4 minutes and 30 seconds.

The above data confirms that PVP-$I_2$ is compatible with this two component prepolymer composition insofar as the resulting prepolymer composition cured within 5 minutes to provide for an antimicrobial polymeric film.

Example 6

The following example illustrates how the antimicrobial effects of a polymeric film of this invention can be determined.

A. Preparation of the Inoculum

Specifically, the surfaces of two TSA plates, 100×15 mm, are inoculated with stock cultures (maintained on TSA slants) with the following microorganisms using a sterile inoculating loop: *Staphylococcus aureus* (ATCC No. 6538) and *Staphylococcus epidermidis* (ATCC No. 12228). The plates are incubated at 30° to 35° C. for 24 hours. The surfaces of two SAB-DEX agar plates are streaked with *Candida albicans* and incubated at 20°–25° C. for 48 hours.

The cultures are harvested with sterile saline. Each culture suspension is collected in a sterile container and sufficient sterile saline is added to reduce the microbial count to obtain a working suspension of approximately $1 \times 10^8$ CFU's per ml.

The specific microorganisms recited above are selected for inclusion herein because they are common human skin pathogens (bacteria and fungus).

B. Inoculation of Plates

Each of the three test microorganisms is used to inoculate individual TSA plates by streaking them with sterile cotton tip applicators saturated with the appropriate suspension. The plates are allowed to dry.

C. Inhibition Study

Films of polymerized prepolymer comprising 0%, 10%, 15%, 20% or 30% iodine polyvinylpyrrolidone complex are formed on filter disks and then cut into approximately 11 to 13 $mm^2$ pieces. The pieces are placed in the center of the appropriate inoculated TSA plates. An untreated filter disk is cut into half, and one-half is placed in the center of the appropriate inoculated TSA plate and the other one-half is place in the center of non-inoculated TSA plates, to serve as a negative control. Two inoculated plates of each microorganism are also used as positive controls without the test article. These plates are then incubated for 3 days at 30° to 35° C. After incubation, the plates are removed and examined for any signs of microbial growth inhibition.

Zones of inhibition extending at least 1 millimeter from the PVP-$I_2$ films evidence that the PVP-$I_2$ is leaching from the film and imparting antimicrobial properties to the film.

From the foregoing description, various modifications and changes in the composition and method will occur to those skilled in the art. All such modifications coming within the scope of the appended claims are intended to be included therein.

What is claimed is:

1. A method for forming an adherent, surface conforming drape at a surgical incision site of a patient which method comprises:

(a) defining a surgical incision site on the patient;

(b) applying a sufficient amount of a composition comprising a polymerizable biocompatible prepolymer to the skin surface at the surgical incision site defined in (a) above so as to cover this site with the composition;

(c) polymerizing the biocompatible prepolymer so as to form a flexible, waterproof, polymer layer which adheres to the area(s) where the composition was applied; and (d) creating an incision through the polymer layer formed in (c) above with the proviso that the biocompatible prepolymer in said composition is not a cyanoacrylate prepolymer.

2. The method according to claim 1 wherein the polymerizable biocompatible prepolymer, in monomeric form, is selected from the group consisting of urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) methacrylate, silicone, styrene, α-methyl styrene, vinyl acetate, one and two component epoxy materials and mixtures thereof.

3. The method according to claim 2 wherein the biocompatible prepolymer is urethane acrylate.

4. The method according to claim 2 wherein the biocompatible prepolymer is ($C_1$–$C_6$ alkyl) methacrylate.

5. The method according to claim 2 wherein the biocompatible prepolymer is ($C_1$–$C_6$ alkyl) acrylate.

6. The method according to claim 2 wherein the biocompatible prepolymer is ($C_1$–$C_6$ hydroxyalkyl) acrylate.

7. The method according to claim 2 wherein the biocompatible prepolymer is ($C_1$–$C_6$ hydroxyalkyl) methacrylate.

8. The method according to claim 7 wherein the compatible antimicrobial agent is polyvinylpyrrolidone iodine.

9. The method according to claim 2 wherein the biocompatible prepolymer is styrene.

10. The method according to claim 2 wherein the biocompatible prepolymer is α-methyl styrene.

11. The method according to claim 2 wherein the biocompatible prepolymer is vinyl acetate.

12. The method according to claim 2 wherein the biocompatible prepolymers are one and two component epoxy materials.

13. The method according to claim 1 wherein said biocompatible prepolymer composition further comprises a biocompatible plasticizer.

14. The method according to claim 1 wherein said biocompatible prepolymer composition further comprises a polymerization inhibitor.

15. The method according to claim 1 wherein said biocompatible prepolymer composition further comprises an antimicrobially effective amount of a compatible antimicrobial agent.

16. The method according to claim 1 wherein the polymer layer has a thickness of no more than about 1 millimeter.

17. The method according to claim 1 which further comprises closing the dermal layer of the surgical incision with a composition comprising a polymerizable biocompatible prepolymer composition or with a cyanoacrylate composition.

* * * * *